United States Patent
Otsuki et al.

(10) Patent No.: US 8,555,699 B2
(45) Date of Patent: Oct. 15, 2013

(54) DETECTOR FOR DETECTING SULFUR COMPONENTS

(75) Inventors: Hiroshi Otsuki, Susono (JP); Hiromasa Nishioka, Susono (JP); Katsuhiko Oshikawa, Tokyo (JP); Yoshihisa Tsukamoto, Susono (JP); Junichi Matsuo, Susono (JP)

(73) Assignee: Toyota Jidosha Kabushiki Kaisha, Toyota (JP)

( * ) Notice: Subject to any disclaimer, the term of this patent is extended or adjusted under 35 U.S.C. 154(b) by 0 days.

(21) Appl. No.: 13/318,430

(22) PCT Filed: May 12, 2010

(86) PCT No.: PCT/JP2010/058397
§ 371 (c)(1),
(2), (4) Date: Nov. 1, 2011

(87) PCT Pub. No.: WO2011/142040
PCT Pub. Date: Nov. 17, 2011

(65) Prior Publication Data
US 2013/0042667 A1    Feb. 21, 2013

(51) Int. Cl.
*G01N 7/00*      (2006.01)
*F01N 3/00*      (2006.01)

(52) U.S. Cl.
USPC ............................................ 73/23.31; 60/277

(58) Field of Classification Search
USPC .............. 73/23.31, 23.32, 23.33; 60/272, 277
See application file for complete search history.

(56) References Cited

U.S. PATENT DOCUMENTS

| | | | | |
|---|---|---|---|---|
| 6,629,453 B1 * | 10/2003 | Surnilla et al. | ............. | 73/114.73 |
| 7,134,274 B2 * | 11/2006 | Asanuma | ......................... | 60/295 |
| 7,533,523 B2 * | 5/2009 | Wang et al. | ..................... | 60/295 |
| 7,669,410 B2 * | 3/2010 | Nagaoka et al. | ................ | 60/286 |
| 8,112,988 B2 * | 2/2012 | Elwart | ............................. | 60/295 |
| 8,156,787 B2 * | 4/2012 | Asanuma et al. | ............. | 73/23.33 |
| 2005/0027431 A1 * | 2/2005 | Todoroki et al. | ............. | 701/105 |
| 2008/0104946 A1 * | 5/2008 | Wang et al. | ..................... | 60/295 |
| 2009/0320451 A1 | 12/2009 | Otsuki et al. | | |

FOREIGN PATENT DOCUMENTS

| | | |
|---|---|---|
| JP | A-2008-175623 | 7/2008 |
| JP | A-2008-286061 | 11/2008 |
| JP | A-2009-030459 | 2/2009 |
| JP | A-2009-138525 | 6/2009 |

OTHER PUBLICATIONS

Jun. 29, 2010 International Search Report issued in International Application No. PCT/JP2010/058397 (with translation).

* cited by examiner

*Primary Examiner* — Hezron E Williams
*Assistant Examiner* — Nathaniel Kolb
(74) *Attorney, Agent, or Firm* — Oliff & Berridge, PLC

(57) ABSTRACT

A detector for detecting sulfur components having a storage portion for storing $SO_X$ and $NO_X$ in the exhaust gas passing through an exhaust passage and a temperature sensor for measuring a temperature of the storage portion. The detector includes a heater for heating the storage portion and determines the current heat capacity (C) of the storage portion on the basis of an increase in (T2−T1) the temperature of the storage portion measured by the temperature sensor and a quantity of heat (QH) generated by the heater when the heater heats the storage portion.

2 Claims, 4 Drawing Sheets

EXHAUST GAS FLOW

EXHAUST GAS FLOW

EXHAUST GAS FLOW

EXHAUST GAS FLOW →

TIME →

DETECTOR FOR DETECTING SULFUR COMPONENTS

TECHNICAL FIELD

The present invention relates to a detector for detecting sulfur components.

BACKGROUND ART

A $SO_X$ concentration sensor for detecting a $SO_X$ concentration in exhaust gas is known. A normal $SO_X$ concentration sensor measures electromotive force produced when $SO_X$ changes into sulfuric acid ion within a solid electrolyte, in order to detect a $SO_X$ concentration in the exhaust gas. However, it is difficult for this $SO_X$ concentration sensor to detect an accurate $SO_X$ concentration when the $SO_X$ concentration in the exhaust gas is low.

A proposed detector for detecting sulfur components cannot detect an instantaneous $SO_X$ concentration but can detect an integrated amount of $SO_X$ passing through the exhaust passage during a given period (for example, refer to Japanese Unexamined Patent Publication No. 2008-175623).

The detector for detecting sulfur components comprises a $SO_X$ storage portion for storing $SO_X$ contained in the exhaust gas, measures a property such as electric resistance, volume or the like of the $SO_X$ storage portion, which changes according to the increase in an amount of $SO_X$ stored in the $SO_X$ storage portion and detects an integrated amount of $SO_X$ passing through the exhaust passage during a given period on the basis of the measured property.

DISCLOSURE OF THE INVENTION

Since it is difficult to accurately measure a change in electric resistance, volume or the like, the above-mentioned detector may be not able to accurately detect an integrated amount of $SO_X$ passing through the exhaust passage during a given period.

If the $SO_X$ storage portion is a storage portion to store $SO_X$ and $NO_X$ in the exhaust gas, in which the more an amount of stored $SO_X$ increases, the more an amount of $NO_X$ that can be stored decreases, and which releases only the stored $NO_X$ and reduces the released $NO_X$ when the air-fuel ratio of the exhaust gas is made stoichiometric or rich, a quantity of heat generated in the reducing reaction of the released $NO_X$ can be calculated on the basis of an increase value of the temperature of the storage portion in the reducing reaction of the released $NO_X$ so that an amount of released $NO_X$ that corresponds to the amount of $NO_X$ that can be stored can be calculated, and thus the current amount of stored $SO_X$ can be estimated in order to finally detect an integrated amount of $SO_X$ passing through the exhaust passage during a given period.

In the case that an integrated amount of $SO_X$ passing through the exhaust passage during a given period is detected in this way, it is necessary to accurately calculate the quantity of heat generated in the reducing reaction of the released $NO_X$ on the basis of the increase value of the temperature of the storage portion in the reducing reaction of the released $NO_X$. Therefore, heat capacity of the storage portion must be accurately predetermined. However, since the heat capacity of the storage portion changes according to the adhesion of ash, such as calcium carbonate or calcium sulfate, particulate, and hydrocarbon with high a boiling point, the predetermined heat capacity may be very different from the current heat capacity. Therefore, an integrated amount of $SO_X$ passing through the exhaust passage during a given period may not be accurately detected.

Accordingly, an object of the present invention is to provide a detector for detecting sulfur components, which can accurately detect an integrated amount of $SO_X$ passing through the exhaust passage in a given period or a value on the basis of the integrated amount.

A first detector for detecting sulfur components of the present invention is provided. The first detector comprises a storage portion for storing $SO_X$ and $NO_X$ in the exhaust gas passing through an exhaust passage, in which the more an amount of stored $SO_X$ increases, the more an amount of $NO_X$ that can be stored decreases, and which releases only the stored $NO_X$ and reduces the released $NO_X$ when the air-fuel ratio in the exhaust gas is made stoichiometric or rich, and a temperature sensor for measuring a temperature of the storage portion, measures an increase in the temperature of the storage portion in the reducing reaction of the released $NO_X$ by the temperature sensor, calculates a quantity of heat generated in the reducing reaction of the released $NO_X$ on the basis of the measured increase in the temperature and heat capacity of the storage portion so that an amount of released $NO_X$ that corresponds to the amount of $NO_X$ that can be stored is calculated in order to estimate a current amount of stored $SO_X$, detects an integrated amount of $SO_X$ passing through the exhaust passage in a given period or a value on the basis of the integrated amount, and is characterized in that the detector comprises a heater for heating the storage portion and determines the current heat capacity of the storage portion on the basis of an increase in the temperature of the storage portion measured by the temperature sensor and a quantity of heat generated by the heater when the heater heats the storage portion.

A second detector for detecting sulfur components of the present invention is provided. The second detector comprises a storage portion for storing $SO_X$ and $NO_X$ in the exhaust gas passing through an exhaust passage, in which the more an amount of stored $SO_X$ increases, the more an amount of $NO_X$ that can be stored decreases, and which releases only the stored $NO_X$ and reduces the released $NO_X$ when the air-fuel ratio in the exhaust gas is made stoichiometric or rich, and a first temperature sensor for measuring a temperature of the storage portion, measures an increase in the temperature of the storage portion in the reducing reaction of the released $NO_X$ by the first temperature sensor, calculates a quantity of heat generated in the reducing reaction of the released $NO_X$ on the basis of the measured increase in the temperature and heat capacity of the storage portion so that an amount of released $NO_X$ that corresponds to the amount of $NO_X$ that can be stored is calculated in order to estimate a current amount of stored $SO_X$, detects an integrated amount of $SO_X$ passing through the exhaust passage in a given period or a value on the basis of the integrated amount, and is characterized in that the detector comprises a second temperature sensor for measuring a temperature in the vicinity of the storage portion and determines a current relationship between the heat capacity of the storage portion and a heat transfer coefficient from the storage portion to the surrounding thereof in order to determine the current heat capacity of the storage portion on the basis of the determined current relationship, because a quantity of heat released from the storage portion from first time to second time while the temperature of the storage portion decreases by releasing heat is represented by on the one hand, the product of an integrated value from the first time to the second time of a temperature difference between the temperature of the storage portion measured by the first temperature sensor and the temperature in the vicinity of the storage portion measured by the second temperature sensor and the heat transfer coefficient, and on the other hand, the product of a decrease in the temperature of the storage portion from the first time to the second time measured by the first temperature sensor and the heat capacity of the storage portion.

According to the first detector for detecting sulfur components of the present invention, the first detector comprises a storage portion for storing $SO_X$ and $NO_X$ in the exhaust gas passing through an exhaust passage, in which the more an amount of stored $SO_X$ increases, the more an amount of $NO_X$ that can be stored decreases, and which releases only the stored $NO_X$ and reduces the released $NO_X$ when the air-fuel ratio in the exhaust gas is made stoichiometric or rich, and a temperature sensor for measuring a temperature of the storage portion, measures an increase in the temperature of the storage portion in the reducing reaction of the released $NO_X$ by the temperature sensor, calculates a quantity of heat generated in the reducing reaction of the released $NO_X$ on the basis of the measured increase in the temperature and heat capacity of the storage portion so that an amount of released $NO_X$ that corresponds to the amount of $NO_X$ that can be stored is calculated in order to estimate a current amount of stored $SO_X$, and detects an integrated amount of $SO_X$ passing through the exhaust passage in a given period or a value on the basis of the integrated amount. The first detector comprises a heater for heating the storage portion and determines the current heat capacity of the storage portion on the basis of an increase in the temperature of the storage portion measured by the temperature sensor and a quantity of heat generated by the heater when the heater heats the storage portion. Accordingly, even if the heat capacity of the storage portion changes with the adhesion of ash or the like in the exhaust gas, the current heat capacity can be accurately determined, and therefore an integrated amount of $SO_X$ passing through the exhaust passage in a given period can be accurately detected.

According to the second detector for detecting sulfur components of the present invention, the second detector comprises a storage portion for storing $SO_X$ and $NO_X$ in the exhaust gas passing through an exhaust passage, in which the more an amount of stored $SO_X$ increases, the more an amount of $NO_X$ that can be stored decreases, and which releases only the stored $NO_X$ and reduces the released $NO_X$ when the air-fuel ratio in the exhaust gas is made stoichiometric or rich, and a first temperature sensor for measuring a temperature of the storage portion, measures an increase in the temperature of the storage portion in the reducing reaction of the released $NO_X$ by the first temperature sensor, calculates a quantity of heat generated in the reducing reaction of the released $NO_X$ on the basis of the measured increase in the temperature and heat capacity of the storage portion so that an amount of released NO that corresponds to the amount of $NO_X$ that can be stored is calculated in order to estimate a current amount of stored $SO_X$, and detects an integrated amount of $SO_X$ passing through the exhaust passage in a given period or a value on the basis of the integrated amount. The second detector comprises a second temperature sensor for measuring a temperature in the vicinity of the storage portion. A quantity of heat released from the storage portion from first time to second time while the temperature of the storage portion decreases by releasing heat is represented by on the one hand, the product of an integrated value from the first time to the second time of a temperature difference between the temperature of the storage portion measured by the first temperature sensor and the temperature in the vicinity of the storage portion measured by the second temperature sensor and heat transfer coefficient from the storage portion to the surrounding thereof, and on the other hand, the product of a decrease in the temperature of the storage portion from the first time to the second time measured by the first temperature sensor and the heat capacity of the storage portion. Accordingly, a current relationship between the heat capacity of the storage portion and the heat transfer coefficient is determined so that the heat capacity and the heat transfer coefficient which are satisfied with the determined relationship can be unconditionally determined. Therefore, the current heat capacity of the storage portion is determined on the basis of the determined relationship. Accordingly, even if the heat capacity of the storage portion changes with the adhesion of ash or the like in the exhaust gas, the current heat capacity can be accurately determined and therefore an integrated amount of $SO_X$ passing through the exhaust passage in a given period can be accurately detected.

BEST MODE FOR CARRYING OUT THE INVENTION

Figure 1:
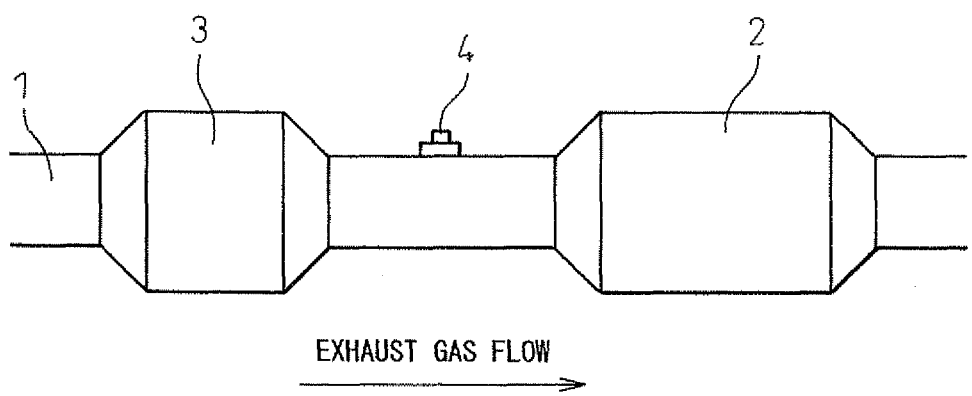
FIG. 1 is a schematic view showing an engine exhaust system in which a detector for detecting sulfur components according to the present invention is arranged.

FIG. 1 is a schematic view showing an engine exhaust system in which a detector for detecting sulfur components according to the present invention is arranged. In FIG. 1, reference numeral 1 is an exhaust passage of an internal combustion engine. The engine is a diesel engine or a direct fuel injection-type spark-ignition engine and performs lean combustion. The exhaust gas of such an engine includes a relatively large amount of $NO_X$ so that a $NO_X$ catalyst device 2 for purifying $NO_X$ is arranged in the exhaust passage 1.

The $NO_X$ catalyst device 2 carries a $NO_X$ storage material and a noble metal catalyst such as platinum Pt. The $NO_X$ storage material is at least one element selected from for example potassium K, sodium Na, lithium Li, cesium Cs, or another alkali metal, barium Ba, calcium Ca, or another alkali earth metal, and lanthanum La, yttrium Y, or another rare earth.

The $NO_X$ catalyst device 2 satisfactorily stores $NO_X$ in the exhaust gas so as to absorb $NO_X$ as nitrate or so as to adsorb $NO_X$ as $NO_2$ when the air-fuel ratio of the exhaust gas is lean, i.e., when the oxygen concentration of the exhaust gas is high. However, the $NO_X$ catalyst device cannot store $NO_X$ without limitation. Accordingly, before the $NO_X$ catalyst device can not almost store further $NO_X$ because an amount of $NO_X$ stored in the $NO_X$ catalyst device almost reaches the largest amount of $NO_X$ that can be stored therein, the air-fuel ratio of the exhaust gas is changed to a stoichiometric air-fuel ratio or a rich air-fuel ratio as the regeneration treatment, namely, the concentration of oxygen of the exhaust gas is lowered. Therefore, the stored $NO_X$ is separated, namely, the absorbed $NO_X$ is released or the adsorbed $NO_2$ is disconnected, and thereafter the separated $NO_X$ is reduced and purified to $N_2$ by reducing materials in the exhaust gas.

Once the $NO_X$ catalyst device 2 stores $SO_X$ in the exhaust gas as sulfate, sulfate is more stable than nitrate so that the stored $SO_X$ cannot be released by the regeneration treatment and an amount of $NO_X$ that can be stored drops (sulfur contamination). Therefore, an S trap device 3 which can store $SO_X$ in the exhaust gas is arranged upstream of the $NO_X$ catalyst device 2 in the exhaust passage 1 to restrain the sulfur contamination of the $NO_X$ catalyst device 2.

The detector for detecting sulfur components 4 according to the present invention is arranged, for example, between the S trap device 3 and the $NO_X$ catalyst device 2, and detects an integrated amount of $SO_X$ passing through the S trap device 3. When the integrated amount of $SO_X$ reaches a set value, it can be determined that it is time to exchange the S trap device 3 for a new one.

Figure 2:
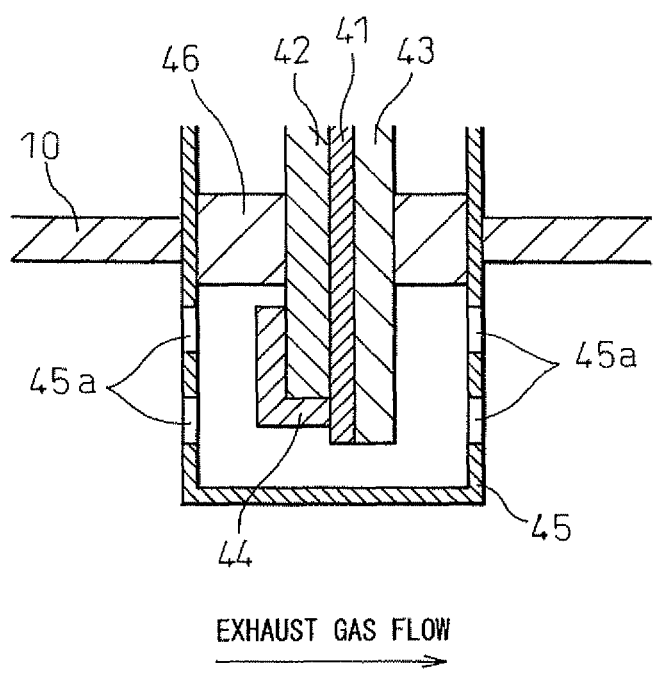
FIG. 2 is a schematic vertical sectional view showing an embodiment of the detector for detecting sulfur components according to the present invention.

FIG. 2 is a schematic vertical sectional view showing an embodiment of the detector for detecting sulfur components 4 according to the present invention. In FIG. 2, reference numeral 10 is the outer wall of the exhaust passage 1. Reference numeral 41 is a base plate of the detector 4. A temperature sensor 42 such as a thermocouple is arranged on one side (preferably exhaust gas upstream side) of the base plate 41. An electric heater 43 is arranged on the other side of the base plate 41. Reference numeral 44 is a storage portion for $NO_X$ and $SO_X$ arranged so as to cover the temperature sensitive portion of the temperature sensor 42. Reference numeral 45 is a cylindrical case which surrounds the detector for detecting sulfur components 4 having the above-construction and goes through the outer wall 10 of the exhaust passage 1.

A plurality of openings 45a is formed on the case 45. The exhaust gas passing through the exhaust passage 1 flows into the case 45 via the openings 45a. Reference numeral 46 is an oxygen pump for supplying oxygen (for example, oxygen in the atmosphere) in the vicinity of the storage portion 44 within the case 45, and the oxygen pump is arranged around the unit of the temperature sensor 42, the base plate 41, and the electric heater 43 to separate the space around the storage portion 44 within the case 45 from the atmosphere chamber. The oxygen pump 46 is made from zirconia or the like. In contrast to a zirconia oxygen sensor, the oxygen pump can make oxygen in the atmosphere move to the vicinity of the storage portion 44 within the case 45 by impressing voltage.

The storage portion 44 stores $NO_X$ and $SO_X$ in the exhaust gas and, for example, can be formed to apply the above-mentioned $NO_X$ storage material and a noble metal catalyst such as platinum Pt on the temperature sensitive portion of the temperature sensor 42.

As mentioned above, the storage portion 44 constructed like this absorb $NO_X$ in the exhaust gas as nitrate and absorb $SO_X$ in the exhaust gas as sulfate instead of $NO_X$. The storage portion 44 has an amount of $NO_X$ that can be stored when $SO_X$ is not stored according to an amount of the $NO_X$ storage material. Sulfate is more stable than nitrate so that an amount of $NO_X$ that can be stored when $SO_X$ is not stored is a standard and the more an amount of stored $SO_X$ increases, the more a current amount of $NO_X$ that can be stored decrease.

On the basis of this relationship, an integrated amount of $SO_X$ passing through the exhaust passage 1 at the position of the detector for detecting sulfur components 4 during a given period can be detected, or an average value of each $SO_X$ concentration in the exhaust gas passing through the exhaust passage 1 at the position of the detector for detecting sulfur components 4 during the given period or an average value of each amount of $SO_X$ in the exhaust gas passing through the exhaust passage 1 at the position of the detector for detecting sulfur components 4 during the given period can be detected as a value on the basis of the integrated amount of $SO_X$.

Figure 3:
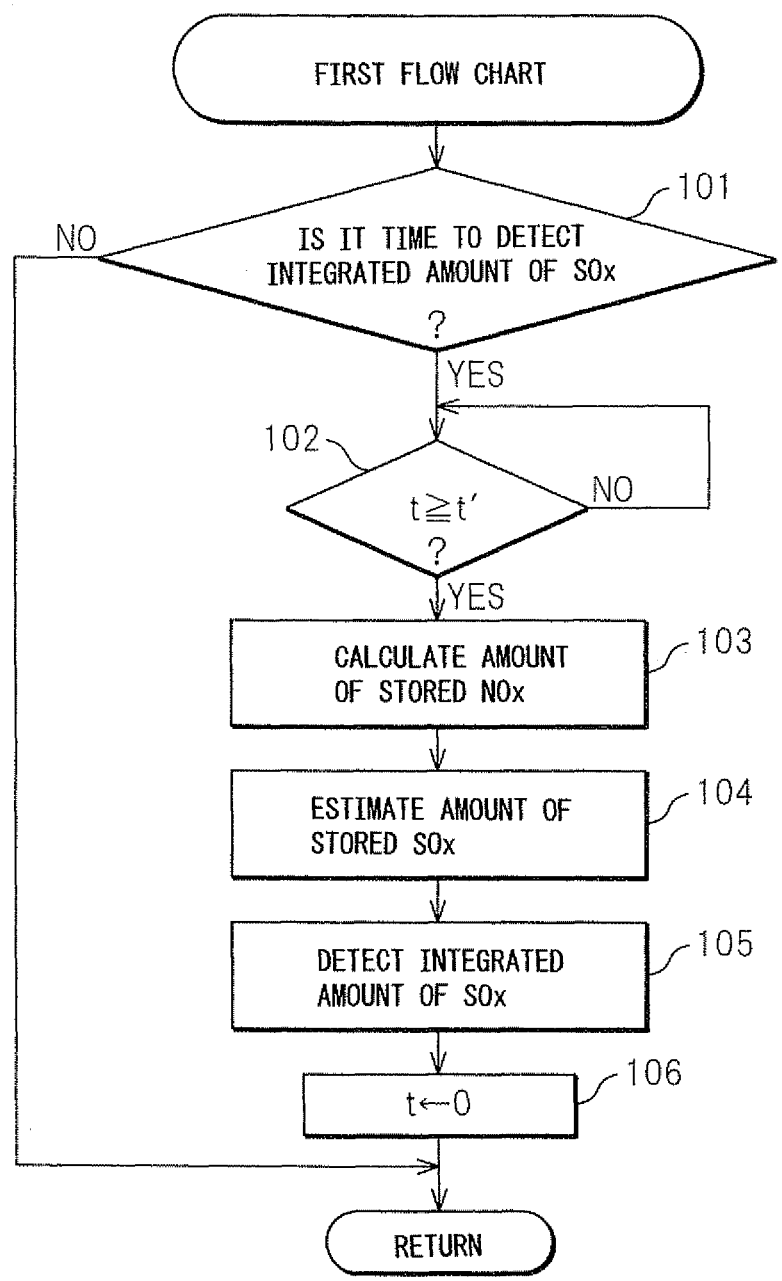
FIG. 3 is a first flow-chart for detecting an integrated amount of $SO_X$ or a value on the basis of the integrated amount by the detector for detecting sulfur components according to the present invention.

FIG. 3 is a flow-chart for detecting an integrated amount of $SO_X$ or a value on the basis of the integrated amount by the detector for detecting sulfur components 4 and is carried out in an electronic control unit (not shown). First, at step 101, it is determined if it is time to detect an integrated amount of $SO_X$. When the result at step 101 is negative, the routine is finished. On the other hand, when it is necessary to detect an integrated amount of $SO_X$ regularly or irregularly, the result at step 101 is positive and the routine goes to step 102.

At step 102, it is determined if an elapsed time (t) which is explained later in detail reaches a set time (t'). This determination is repeated until the result thereof is positive. When the result at step 102 is positive, an air-fuel ratio of the exhaust gas in the vicinity of the storage portion 44 is made rich to lower the oxygen concentration in the vicinity of the storage portion 44. Therefore, $NO_X$ is released from the storage portion 44 and is reduced as follows.

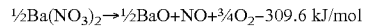

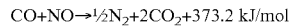

Thus, a quantity of heat of about 490 kJ is produced for 1 mol of NO. Therefore, an increase value of temperature $\Delta T$ (Ta−Tb) between a maximum temperature (Ta) of the storage portion after the air-fuel ratio of the exhaust gas in the vicinity of the storage portion 44 is changed to rich and a temperature (Tb) of the storage portion 44 before the air-fuel ratio of the exhaust gas in the vicinity of the storage portion 44 is changed to rich is measured by the temperature sensor 42. At step 103, a quantity of heat (Q) generated in the reducing reaction of the released $NO_X$ is calculated by multiplying this increase value of the temperature ($\Delta T$) by the heat capacity (C) of the storage portion and an amount of $NO_X$ stored in the storage portion 44 (mol) (=Q/490 kJ) is calculated on the basis of the calculated quantity of heat (Q). When the measurement of the increase value of the temperature ($\Delta T$) is finished, the air-fuel ratio in the exhaust gas is returned to lean of normal engine operations.

When the amount of stored $NO_X$ is less than the amount of $NO_X$ that can be stored when $SO_X$ is not stored, $SO_X$ is stored in the storage portion 44 and at step 104, a current amount of stored $SO_X$ is estimated on the basis of the difference between the amount of $NO_X$ that can be stored and the amount of stored $NO_X$.

A given rate of an amount of $SO_X$ passing through the exhaust passage 1 at the position of the detector for detecting sulfur components 4 is stored in the storage portion 44 of the detector 4. Therefore, at step 105, an integrated amount of $SO_X$ passing through the exhaust passage 1 at the position of the detector 4 during the given period is detected on the basis of the current amount of stored $SO_X$. Next, at step 106, the elapsed time (t) is reset to 0 and the routine is finished.

In the present flow chart, to estimate accurately the amount of $SO_X$ stored in the storage portion 44 at step 104, the amount of $NO_X$ stored in the storage portion 44 calculated at step 103 must be equal to the current amount of $NO_X$ that can be stored which is decreased by the stored $SO_X$. Namely, when the amount of $SO_X$ stored in the storage portion 44 at step 104 is estimated, it is required that the current amount of $NO_X$ that can be stored is stored in the storage portion 44. If the amount of stored $SO_X$ is estimated on the basis of the amount of stored $NO_X$ when the current amount of $NO_X$ that can be stored is not stored in the storage portion, the estimated amount of stored $SO_X$ becomes more than an actual amount.

In the present flow chart, when the elapsed time (t) does not reach the set time (t'), there is some possibility that the current amount of $NO_X$ that can be stored is not stored in the storage portion 44, the result at step 102 is negative so that the processes after step 103 including the estimation of the amount of stored $SO_X$ for detecting the integrated amount of $SO_X$ are not carried out.

The elapsed time (t) is reset to 0 when the engine is started initially or is reset to 0 at step 106 of the present flow-chart. In addition to these, the elapsed time (t) is reset to 0 when all of the $NO_X$ is released from storage portion 44. For example, in the regeneration treatment of the $NO_X$ catalyst device 2, the air-fuel ratio of the exhaust gas is changed to rich and all of the $NO_X$ is released from the storage portion 44 so that the elapsed time (t) is reset to 0 when the regeneration treatment is finished. On the other hand, to reset the integrated amount of $SO_X$, all of the stored $SO_X$ is released from the storage portion 44. In this case, all of the $NO_X$ is also released from the storage portion 44 so that the elapsed time (t) is reset to 0.

Incidentally, the current amount of $NO_X$ that can be stored in the storage portion 44 is changed in accordance with the temperature of the storage portion 44. For example, in the storage portion 44 formed from the $NO_X$ storage material (Ba), the amount of $NO_X$ that can be stored when $SO_X$ is not stored become large when the temperature of the storage portion 44 is, for example, 350 degrees C. and over.

Thus, to accurately estimate the amount of stored $SO_X$ for detecting the integrated amount of $SO_X$, it is preferable that the temperature of the storage portion 44 when the current amount of $NO_X$ that can be stored in the storage portion 44 is detected corresponds with a set temperature of the storage portion 44 at which the amount of $NO_X$ that can be stored when $SO_X$ is not stored is determined as the standard. When the temperature of the storage portion 44 is out of the set temperature range including this set temperature, it is preferable to prohibit the estimation of the amount of stored $SO_X$ for detecting the integrated amount of $SO_X$. When the temperature of the storage portion 44 becomes out of the set temperature range and the amount of $NO_X$ that can be stored decreases by the changing of the temperature of the storage portion 44, if the amount of stored $SO_X$ is estimated on the basis of the amount of stored $NO_X$, the estimated amount of stored $SO_X$ becomes more than the actual amount.

Incidentally, in the first flow-chart, to accurately detect an integrated amount of $SO_X$ passing through the exhaust passage during a given period, it is necessary to accurately calculate a quantity of heat generated in the reducing reaction of $NO_X$ released from the storage portion 44. Therefore, the heat capacity (C) of the storage portion used in this calculation must be accurate.

Since the heat capacity (C) of the storage portion changes with the adhesion of ash such as calcium carbonate or calcium sulfate or the like in the exhaust gas, unless the heat capacity is updated according to the current state, the heat capacity (C) of the storage portion cannot be made accurate.

Figure 4:
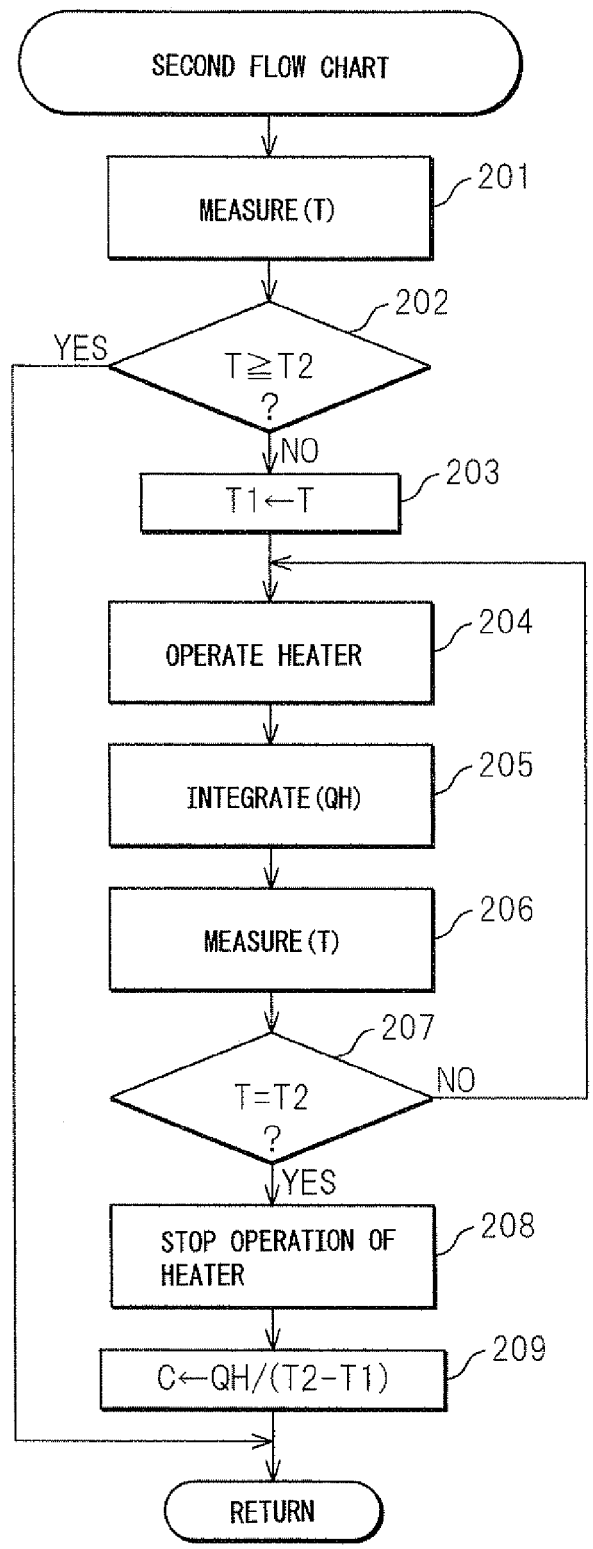
FIG. 4 is a second flow-chart for updating the heat capacity of the storage portion used in the first flow-chart.

FIG. 4 is a second flow-chart for maintaining the temperature (T) of the storage portion 44 within the set temperature range (>=T2) and for updating the heat capacity of the storage portion. First, at step 201, the temperature (T) of the storage portion 44 is measured by the temperature sensor 42. Next, at step 202, it is determined if the temperature (T) of the storage portion 44 is the set temperature (T2) (for example, 350 degrees C.) and over. When the result at step 202 is positive, the temperature (T) of the storage portion 44 is within the set temperature range (>=T2), it is not necessary to operate the electric heater 4, and the routine is finished.

On the other hand, when the result at step 202 is negative, the current temperature (T) of the storage portion 44 is memorized as (T1) at step 203. Next, at step 204, the electric heater 43 is operated. At step 205, a quantity of heat (QH) generated by the electric heater 43 is integrated. Next, at step 206, the temperature (T) of the storage portion 44 is measured by the temperature sensor 42. At step 207, it is determined if the temperature (T) of the storage portion 44 reaches the set temperature (T2). When the result at step 207 is negative, the processes from step 204 to step 206 are repeated.

When the temperature (T) of the storage portion 44 reaches the set temperature (T2), the result at step 207 is positive and therefore the operation of the electric heater 43 is stopped at step 208. At step 209, the current heat capacity (C) of the storage portion 44 is calculated by dividing the quantity of heat (QH) generated by the electric heater 42 integrated at step 205 in order to elevate the temperature (T1) of the storage portion 44 from (T1) to (T2) by the increase value of the temperature (T2−T1), and the heat capacity (C) of the storage portion 44 used at step 103 of the first flow-chart is updated.

Thus, if the heat capacity (C) of the storage portion changes with the adhesion of ash such as calcium carbonate or calcium sulfate or the like in the exhaust gas, the heat capacity (C) of the storage portion can be made accurate because the heat capacity (C) of the storage portion 44 is calculated on the basis of the increase value (T2−T1) of the temperature of the storage portion 44 when the electric heater 43 actually heats the storage portion and the quantity of heat (QH) generated by the electric heater and the heat capacity is updated.

The update of the heat capacity (C) of the second flow-chart is always carried out with the operation of the electric heater 43 when the temperature (T) of the storage portion 44 is lower than the set temperature (T2). The present invention is not limited by the update in this way. The frequency of update of the heat capacity may be decreased (for example every engine start).

Figure 5:
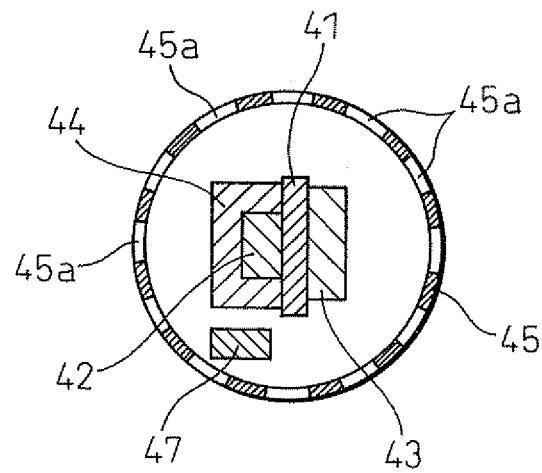
FIG. 5 is a schematic horizontal sectional view showing another embodiment of the detector for detecting sulfur components according to the present invention.

FIG. 5 is a schematic horizontal sectional view showing another embodiment of the detector for detecting sulfur components according to the present invention. In FIG. 5, the same members as the embodiment shown in FIG. 2 comprises have the same reference numerals. The difference between the present embodiment and the embodiment shown in FIG. 2 is that another temperature sensor 47 is arranged in the present embodiment in order to measure a temperature in the vicinity of the storage portion 44.

Figure 6:
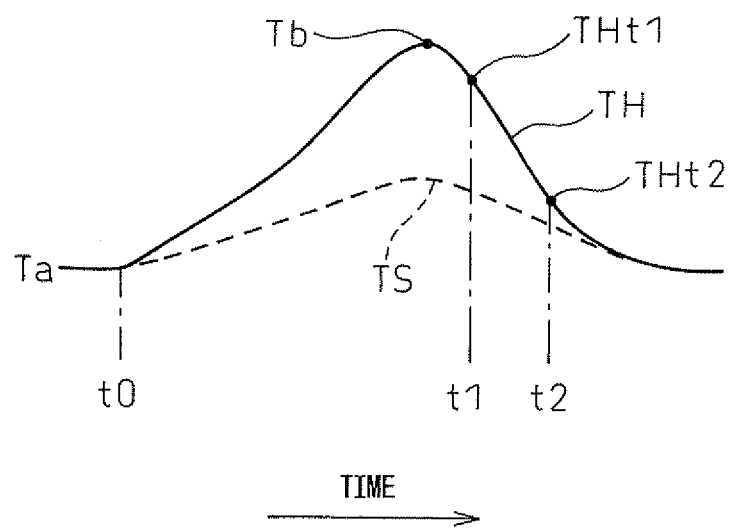
FIG. 6 is a time-chart showing a change of the temperature of the storage portion and a change of the temperature in the vicinity of the storage portion when $NO_X$ is released and the released $NO_X$ is reduced in order to detect an integrated amount of $SO_X$.

Once $NO_X$ is released and is reduced at time (t0) by making the air-fuel ratio of exhaust gas rich in order to detect an integrated amount of $SO_X$, the temperature of the storage portion 44 which is (Ta) at the time (t0) changes as shown by the solid line in FIG. 6 and the temperature in the vicinity of the storage portion 44 which is (Ta) at the time (t0) changes as shown by the dotted line in FIG. 6.

As explained regarding step 103 of the first flow-chart, the temperature of the storage portion 44 gradually decreases by releasing heat after the temperature of the storage portion 44 reaches the maximum temperature (Tb) by reducing the released $NO_X$.

Thus, while the temperature of the storage portion 44 decreases, the temperature (TH) of the storage portion 44 is measured by the temperature sensor and the temperature (TS) in the vicinity of the storage portion 44 is measured by another temperature sensor 47. The temperature of the storage portion 44 measured by the temperature sensor 42 at any first time (t1) is (THt1) and the temperature of the storage portion 44 measured by the temperature sensor 42 at any second time (t2) after the first time (t1) is (THt2). In this case, with using heat transfer coefficient (K) from the storage portion 44 to the surrounding thereof, a quantity of heat (QR) released from the storage portion between the first time (t1) and the second time (t2) is represented by the product of an integrated value from the first time (t1) to the second time (t2) of a temperature difference between the temperature (TH) of the storage portion 44 and the temperature (TS) in the vicinity of the storage portion 44 and the heat transfer coefficient (K) around the storage portion, as shown by next expression (1).

$$QR = K \cdot \int (TH-TS) dt \qquad (1)$$

On the other hand, by using the heat capacity (C) of the storage portion 44, a quantity of heat (QR) released from the storage portion between the first time (t1) and the second time (t2) is represented by the product of a decrease value (THt1−THt2) of the temperature of the storage portion 44 from the first time (t1) to the second time (t2) and the heat capacity (C) of the storage portion 44, as shown by next expression (2).

$$QR = (THt1-THt2) \cdot C \qquad (2)$$

Since the right side of expression (1) is equal to the right side of expression (2), as a relationship between the current heat capacity (C) of the storage portion 44 and the heat transfer coefficient (K) from the storage portion 44 to the surrounding thereof, for example, (C/K) is represented by next expression (3) and is a known value.

$$C/K = (\int (TH-TS) dt)/(THt1-THt2) \qquad (3)$$

The more the ash or the like adheres on the storage portion 44, the larger the heat capacity (C) is, and the smaller the heat transfer coefficient is. Thus, the heat capacity (C) and the heat transfer coefficient (K) change so as to correlate each other. Therefore, when a ratio (C/K) of the heat capacity (C) to the heat transfer coefficient (K) is determined, the heat capacity (C) and the heat transfer coefficient (K) so as to give this ratio can be unconditionally determined. Accordingly, for example, a combination of the heat capacity (C) and the heat transfer coefficient (K), which are satisfied with each value of the ratios (C/K) changing according to the adhesion of the ash or the like, can be preset in a map.

Thus, even if the heat capacity of the storage portion 44 changes with the adhesion of ash such as calcium carbonate or calcium sulfate or the like in the exhaust gas, the current heat capacity (C) of the storage portion 44 can be determined and updated by measuring the temperature of the storage portion 44 and the temperature in the vicinity of the storage portion 44 while the temperature of the storage portion 44 decreases and therefore the heat capacity (C) of the storage portion 44 can be made accurate. It is preferable for the update of the heat capacity (C) to be carried out every reduction of the $NO_X$ released from the storage portion 44. The updated heat capacity can be preferably used to calculate the quantity of heat generated in the next reducing reaction of $NO_X$. Even if $NO_X$ is not released to make the air-fuel ratio of the exhaust gas rich, the current heat capacity (C) can be determined as mentioned above while the temperature of the storage portion 44 decreases after the temperature of storage portion 44 is elevated by the electric heater 43.

Incidentally, in case that the storage portion 44 of the detector for detecting sulfur components 4 stores $NO_X$ in the exhaust gas as nitrate, if oxygen is supplied in the vicinity of the storage portion 44, NO in the exhaust gas is oxidized to $NO_2$ by the supplied oxygen and is easily stored in the storage portion 44 as nitrate.

In accordance with the engine operating conditions, the oxygen concentration in the exhaust gas flowing into the case 45 becomes relatively low. Therefore, except during the air-fuel ratio of the exhaust gas is intentionally made rich in the regeneration treatment of $NO_X$ catalyst device 2, the process for releasing $NO_X$ from the storage portion 44 mentioned above, or the like, the oxygen pump 46 is preferably operated to supply oxygen in the vicinity of the storage portion 44 such that NO in the exhaust gas is easily stored in the storage portion 44. Particularly, the air-fuel ratio of the exhaust gas in the vicinity of the storage portion 44 is preferably made 40 and over.

In the first flow-chart of FIG. 3, the elapsed time (t) for storing $NO_X$ in the storage portion 44 can be changed to a running distance. When the air-fuel ratio of the exhaust gas is made rich in the regeneration treatment of the $NO_X$ catalyst device 2 and the detection of the amount of $NO_X$ stored in the storage portion 44, the air-fuel ratio of combustion in the engine may be made rich, additional fuel may be supplied into cylinder in exhaust stroke or expansion stroke, or fuel may be supplied to the exhaust gas in the exhaust passage 1.

LIST OF REFERENCE NUMERALS

1: exhaust passage
2: $NO_X$ catalyst device
3: S trap device
4: detector for detecting sulfur components
42: temperature sensor
43: electric heater
44: storage portion
47: another temperature sensor

The invention claimed is:

1. A detector for detecting sulfur components comprising a storage portion for storing $SO_X$ and $NO_X$ in the exhaust gas passing through an exhaust passage, in which the more an amount of stored $SO_X$ increases, the more an amount of $NO_X$ that can be stored decreases, and which releases only the stored $NO_X$ and reduces the released $NO_X$ when the air-fuel ratio in the exhaust gas is made stoichiometric or rich, and a temperature sensor for measuring a temperature of said storage portion, measuring an increase in the temperature of said storage portion in the reducing reaction of the released $NO_X$ by said temperature sensor, calculating a quantity of heat generated in the reducing reaction of the released $NO_X$ on the basis of the measured increase in the temperature and heat capacity of said storage portion so that an amount of released $NO_X$ that corresponds to the amount of $NO_X$ that can be stored is calculated in order to estimate a current amount of stored $SO_X$, and detecting an integrated amount of $SO_X$ passing through said exhaust passage in a given period or a value on the basis of said integrated amount, wherein said detector comprises a heater for heating said storage portion and determines the current heat capacity of said storage portion on the basis of an increase in the temperature of said storage portion measured by said temperature sensor and a quantity of heat generated by said heater when said heater heats said storage portion.

2. A detector for detecting sulfur components comprising a storage portion for storing $SO_X$ and $NO_X$ in the exhaust gas passing through an exhaust passage, in which the more an amount of stored $SO_X$ increases, the more an amount of $NO_X$ that can be stored decreases, and which releases only the stored $NO_X$ and reduces the released $NO_X$ when the air-fuel ratio in the exhaust gas is made stoichiometric or rich, and a first temperature sensor for measuring a temperature of said storage portion, measuring an increase in the temperature of said storage portion in the reducing reaction of the released $NO_X$ by said first temperature sensor, calculating a quantity of heat generated in the reducing reaction of the released $NO_X$ on the basis of the measured increase in the temperature and heat capacity of said storage portion so that an amount of released $NO_X$ that corresponds to the amount of $NO_X$ that can be stored is calculated in order to estimate a current amount of stored $SO_X$, and detecting an integrated amount of $SO_X$ passing through said exhaust passage in a given period or a value on the basis of said integrated amount, wherein said detector comprises a second temperature sensor for measuring a temperature in the vicinity of said storage portion and determines a current relationship between the heat capacity of said storage portion and a heat transfer coefficient from said storage portion to the surroundings thereof in order to determine the current heat capacity of said storage portion on the basis of the determined current relationship, because a quantity of heat released from said storage portion from first time to second time while the temperature of said storage portion decreases by releasing heat is represented by on the one hand, the product of an integrated value from said first time to said second time of a temperature difference between the temperature of said storage portion measured by said first temperature sensor and the temperature in the vicinity of said storage portion measured by said second temperature sensor and the heat transfer coefficient, and on the other hand, the product of a decrease in the temperature of said storage portion from said first time to said second time measured by said first temperature sensor and the heat capacity of said storage portion.

\* \* \* \* \*